United States Patent [19]

Kitaura et al.

[11] Patent Number: 4,921,799
[45] Date of Patent: May 1, 1990

[54] FERMENTATION METHOD

[75] Inventors: Shinko Kitaura; Yoshimasa Takahara, both of Kobe; Shiro Nagai, Hiroshima; Naomichi Nishio, Higashihiroshima, all of Japan

[73] Assignee: Kabushiki Kaisha Kobe Seiko Sho, Kobe, Japan

[21] Appl. No.: 93,497

[22] PCT Filed: Mar. 13, 1987

[86] PCT No.: PCT/JP87/00156
§ 371 Date: Jul. 17, 1987
§ 102(e) Date: Jul. 17, 1987

[30] Foreign Application Priority Data

Mar. 14, 1986 [JP] Japan .................................. 61-54696
Mar. 14, 1986 [JP] Japan .................................. 61-54697

[51] Int. Cl.$^5$ .............................................. C12P 5/02
[52] U.S. Cl. ................................... 435/167; 435/166; 435/157
[58] Field of Search ............... 435/136, 166, 167, 170, 435/174

[56] References Cited

U.S. PATENT DOCUMENTS

| | | | |
|---|---|---|---|
| 4,425,432 | 1/1984 | Zeikus et al. | 435/140 |
| 4,506,012 | 3/1985 | Reed | 435/139 |
| 4,571,384 | 2/1986 | Morita et al. | 435/166 |
| 4,632,758 | 12/1986 | Whittle | 435/167 |

FOREIGN PATENT DOCUMENTS 54-40090 3/1983 Japan .
223496 12/1983 Japan .
59-98694 6/1984 Japan .

OTHER PUBLICATIONS

S. Y. Eguchi et al, Appln. Microbiol. Biotechnol, 22, 148-151 (1985), Formic Acid Production from $H^2$ and Bicarbonate by a Formateutilizing . . .

Primary Examiner—Barry S. Richman
Assistant Examiner—T. J. Wallen
Attorney, Agent, or Firm—Oblon, Spivak, McClelland, Maier & Neustadt

[57] ABSTRACT

This invention provides a new fermentation method and apparatus for the same for producing a substance by a microbial action from a gaseous substrate, wherein the cells of a microorganism fixed to a carrier are held in a reactor, an aqueous solution is fed to said reactor so as to moisten at least part of the surface of said microbial cells, and said gaseous substrate is forced to pass through the interstices of said microbial cells, thereby causing direct reaction between the microorganism and the gaseous substrate and effecting efficient biosynthesis of methane, formic acid and other substances.

5 Claims, 3 Drawing Sheets

FERMENTATION METHOD

TECHNICAL FIELD

This invention relates to a new method of producing a substance by microbial action. More particularly, it relates to the biosynthesis of a substance from a gaseous material using fixed cells of a microorganism.

Hence, the technique disclosed in this invention will play an important role in the field of biotechnology, such as fermentation, microbial, enzyme and food engineering. Methane and other substances produced by the method of this invention can be converted into methanol, hydrogen cyanide, acetylene and other organic chemicals of industrial importance; in this respect, the technique of this invention will be of great importance also in the chemical industry.

DESCRIPTION OF THE PRIOR ART

No industrial system is so far known for the manufacture of methane by microbial action. Methane has been obtained as a byproduct liberated by anaerobic fermentation in the sewage and night soil treatment, or by decay of compost and other organic wastes. In these processes, however, organic polymers are decomposed by the action of microorganisms contained in sludge into low-molecular substances, ultimately giving methane—processes quite different from the biosynthesis of methane from a gaseous material of low molecular weight.

Recently a system has been developed for the manufacture of methane using an apparatus as shown in FIG. 2. Cells of a methanogen 12 are suspended in a liquid medium 11 containing nitrogen sources, inorganic salts and other auxiliary nutrients, carbon dioxide and hydrogen gases are forced into said liquid medium from the outside of fermentor 13, the bubbles of gases 19 from orifices 18 are finely dispersed by mechanical agitation with agitator blades 14 (fermentator with aeration and agitation) or by the use of a draft tube 16 (fermentator of bubble-tower type 17), thereby prolonging the retention time of gases in the liquid medium, accelerating solution of the carbon dioxide and hydrogen gases into the liquid medium, and causing a biochemical reaction by said methanogen to take place. This system is not intended for biosynthesis of methane from the material gases through direct gas-phase reaction; nor can it be put to practical use because of the low yield of methane and other disadvantages.

No industrial fermentation process has also been established in which a product is manufactured by allowing gaseous substrate to act directly upon fixed cells of a microorganism.

For example, a technique was proposed in which formic acid is produced by supplying a gaseous material to an aqueous suspension of microbial cells [S. Y. Eguchi et al., Appl. Microbiol. Biotechnol., 22, 148–151 (1985)]. This system, too, is not intended for biosynthesis from the material gases through direct gas-phase reaction; nor can it be applied to commercial production because of the low yield of formic acid and other disadvantages.

Thus no technique has so far been established in which biosynthesis is effected by direct supply of gaseous substrate to the cells of a microorganism, not to mention the use of fixed microbial cells.

PROBLEMS TO BE SOLVED

Figure 1:
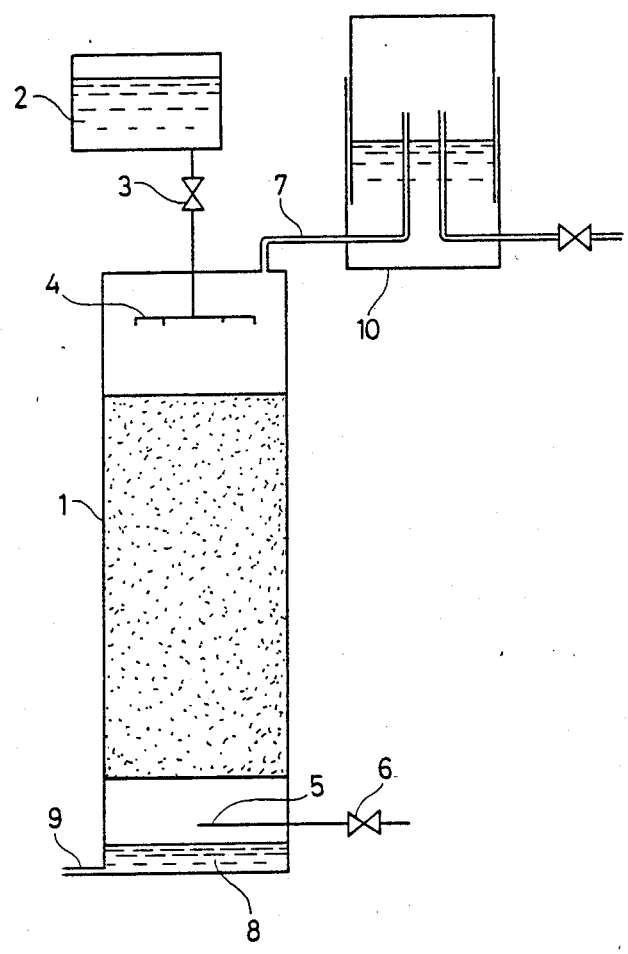
FIG. 1 illustrates an example of apparatuses used in the method of this invention.
Figure 2A:
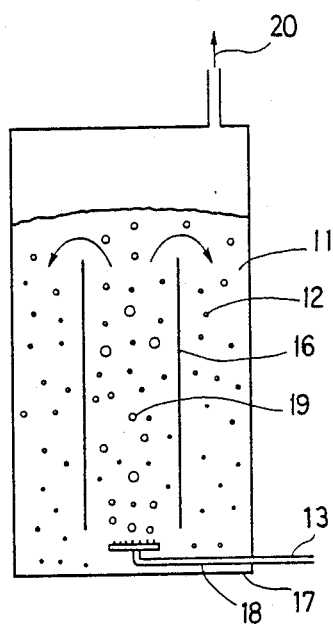
FIG. 2 is a conventional methane fermentator.
Figure 2B:
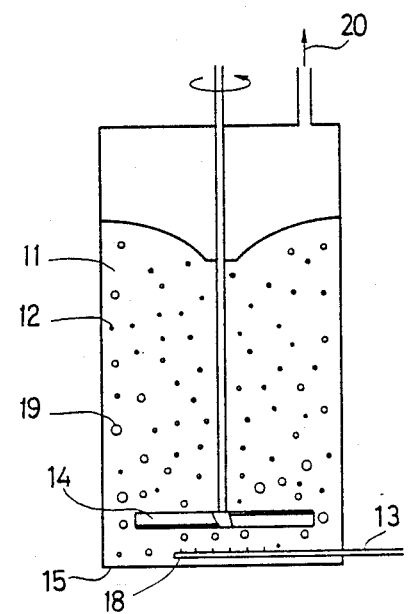

The object of this invention is to establish an industrial system for the direct biosynthesis from gaseous substrate. We first started with the study on the systems using a fermentor of aeration/agitation type or of bubble-tower type, but these conventional systems turned out to have disadvantages as enumerated below.

1. The fermentor of aeration/agitation type requires much power for mechanical agitation.

2. There is a limit to the solution speed of each substrate gas. If it is supplied at a speed exceeding that limit, most of the gas reaches the surface of the liquid unconsumed by the microorganism, resulting in very low contact efficiency.

3. The substrate gas cannot be supplied at a speed comparable to the substrate-consuming speed of microorganism, making continuous operation difficult.

4. A large reactor has to be used because a huge volume of liquid and a large liquid depth are required; hence, it is impossible to make the whole facility compact.

What is decisive is that none of these conventional systems allows direct biosynthesis of objective substances from gaseous substrates.

SUMMARY OF THE INVENTION

This invention is aimed at developing a new industrial system which is free from the problems mentioned above and is able to mass-produce objective substances at low costs.

Comprehensive studies along this line have led us to find that a high product yield cannot be achieved without increasing the concentration of each feed gas and enhancing its contact efficiency with the microorganism used. The gas concentration cannot be sufficiently increased so long as it is dissolved in a liquid medium or supplied in the form of bubbles as in conventional processes. We then hit upon a novel idea that biosynthesis be effected by bringing a gaseous substrate into direct contact with microbial cells in gaseous form.

Further studies have demonstrated that this innovative idea can be put in practice on an industrial scale if fixed cells of a microorganism are used. This invention was accomplished based on these findings.

This invention will be detailed below by referring to the apparatus shown in FIG. 1 (an example of apparatuses used for practicing this invention).

Reactor 1 holds fixed microbial cells. Cell fixation is effected by usual methods; any known carrier-fixing technique may be used.

Microbial cells may be previously fixed in any desired form (spherical, cylindrical, granular, etc.), followed by charging in the reactor, or may be fixed directly to the wall of reactor. Alternatively, a large number of hollow fibers having microbial cells fixed to the internal and/or external surfaces thereof are filled in the reactor; or at least one porous plate with microbial cells fixed thereto is set vertical or horizontal in the reactor; or a large number of small columns packed with fixed microbial cells are filled in the reactor.

Any species of microorganisms that are capable of producing objective substances from gaseous substrates may be used for the purpose of this invention. Illustrative examples include a Gram-positive methanogen, strain HU, isolated from digested sludge in the sewage treatment plant of Hiroshima City (stocked in Nagai Laboratory, Department of Technology, Hiroshima University; readily supplied upon request), species of Methanobacterium (e.g., *M. thermoautotrophicum* and *M. formicicum*), species of Methanococcus (e.g., *M. vanielii*) and species of Methanosaricina (e.g., *M. barkerii*), which may be employed either alone or in combination. These microbial cells may also be used without being isolated; liquid culture, wet cakes, activated sludge or digested sludge containing the same may be directly fixed to a carrier for use in the method of this invention.

Aqueous solution 2 containing nitrogen sources, inorganic salts and other auxiliary nutrients is allowed to spray, drop or flow down through orifices 4 under the control by regulation valve 3 onto the carrier to which a microorganism or a group of microorganisms has been fixed. As required, this nutrient solution may be previously held by the carrier. When the microorganism used demands, other than gaseous substrates (such as carbon dioxide, hydrogen and carbon monoxide) specific compounds, these may be also contained in the nutrient solution. Thus the method of this invention can be applied to any types of microorganisms.

In the method of this invention, methane gas will be produced if, for example, the nutrient solutions used in Examples 1 through 3 are employed, while the nutrient solution of Example 4 yields formic acid.

In parallel with the addition of nutrient solution 2, a gaseous substrate of proper composition is supplied through regulation valve 6 and pipe 5 at the bottom of reactor, and brought into contact with the microbial cells fixed to the carrier and the nutrient solution. The type and composition of gaseous substrate should be properly selected depending upon the microorganism used. For the methanogen strain HU, for example, a mixture of hydrogen and carbon dioxide gases are used, the $H_2/CO_2$ ratio preferably being higher than 1. It is advisable that a gas analyzer (not shown in the figure) be installed at the product gas outlet 7 to analyze the composition of product gas, thereby optimizing the mixing ratio and feed rate of feed gases by operating regulation valve 6 provided at the gas inlet. The same is true of the other types of microorganisms.

Reactor 1 may be provided with a jacket through which hot water or gas is allowed to flow or heater wires are installed to accelerate the biochemical reaction. It is also possible to supply the gaseous substrate at the top of reactor and to withdraw the product gas from its bottom. The aqueous solution which collects in tank 8 may be recycled back to solution tank 2 from solution outlet 9 through a pump and piping (not shown in the figure) to further reduce the production cost. When the reaction product is soluble in water, it can be recovered from the aqueous solution which collects in tank 8 after withdrawal through outlet 9. When desired, the reactor may be held under an elevated pressure to have more gases kept dissolved in the nutrient solution, thereby increasing the reaction rate. The reaction product can be obtained with the highest yield if the reactor is enclosed and the quantity of gaseous substrate in the reactior is kept optimized for the fixed microorganism.

When the reaction product is a gas, it is introduced through gas outlet 7 into gas tank 10; and when the reaction product is soluble in water, it is recovered from the aqueous solution which collects in tank 8.

EXAMPLES 1 through 3

The strain HU (isolated and stocked in Nagai Laboratory, Department of Technology, Hiroshima University) was each fixed to Zeolite, foamed brick and an inorganic porous material (grain size: 7.1 to 12.6 mm) through adsorption.

Each of the fixed methanogen thus obtained was filled in a reactor (capacity: 75 ml) as shown in FIG. 1, and methane fermentation was conducted under the conditions given below using the apparatus of FIG. 1. Hot water was circulated through the jacket around the reactor to maintain the internal temperature at the optimum level (37° C.).

Capacity of reactor: 75 ml
Fermentation temperature: 37° C.

| Amount of fixed microbial cells ( for each run ) | | |
|---|---|---|
| EXAMPLE 1 | Zeolite | 0.675 g-dry cell |
| EXAMPLE 2 | Foam brick | 0.643 g-dry cell |
| EXAMPLE 3 | Inorganic cellular material | 0.604 g-dry cell |

Feed rate of nutrient solution: 25 to 30 ml/day
Feed rate of gaseous substrate: 4760 ml/day
Composition of gaseous substrate: $H_2$ 81.5%, $CO_2$ 18.5%

TABLE 1

| Composition of Nutrient Solution | |
|---|---|
| $NH_4Cl$ | 0.9 g/l |
| $NaH_2PO_4.2H_2O$ | 3 g/l |
| $K_2HPO_4$ | 7 g/l |
| $MgCl_2.6H_2O$ | 0.36 g/l |
| $Na_2S.9H_2O$ | 0.5 g/l |
| Trace metal solution[1] | 9 ml/l |
| Vitamin solution[2] | 5 ml/l |

[1]Trace metal solution
| EDTA | 1 g/l |
| $Fe_3(PO_4)_2.8H_2O$ | 1.02 g/l |
| $MnCl_2.4h_2O$ | 0.1 g/l |
| $CoCl_2.6H_2O$ | 0.17 g/l |
| $ZnCl_2$ | 0.1 g/l |
| $CaCl_2$ | 0.02 g/l |
| $H_3BO_3$ | 0.019 g/l |
| $Na_2MoO_4.2H_2O$ | 0.01 g/l |

[2]Vitamin solution
| Biotin | 2 mg/l |
| Pyridoxine-HCl | 10 mg/l |
| Folic acid | 2 mg/l |
| Riboflavin | 5 mg/l |
| Thiamine | 5 mg/l |
| Nicotinic acid | 5 mg/l |
| Ca pantothenate | 5 mg/l |
| Vitamin $B_{12}$ | 0.1 mg/l |
| α-lipoic acid | 5 mg/l |
| p-Aminobenzoic acid | 5 mg/l |

The results obtained are summarized below.

| Composition of product gas | | $H_2$ | $CO_2$ | $CH_4$ |
|---|---|---|---|---|
| EXAMPLE 1 | Zeolite | 45.2 | 0 | 54.8 |
| EXAMPLE 2 | Foam brick | 46.5 | 0.8 | 52.7 |
| EXAMPLE 3 | Inorganic porous material | 43.5 | 0 | 56.5 |

As is apparent from the above data, the method of this invention allows direct biosynthesis of methane from hydrogen and carbon dioxide gases. High-purity methane was effcently produced, with little, if any, carbon dioxide being detected in the product gas.

EXAMPLE 4

(Production of formic acid from $H_2$ and $CO_2$)

Figure 3:
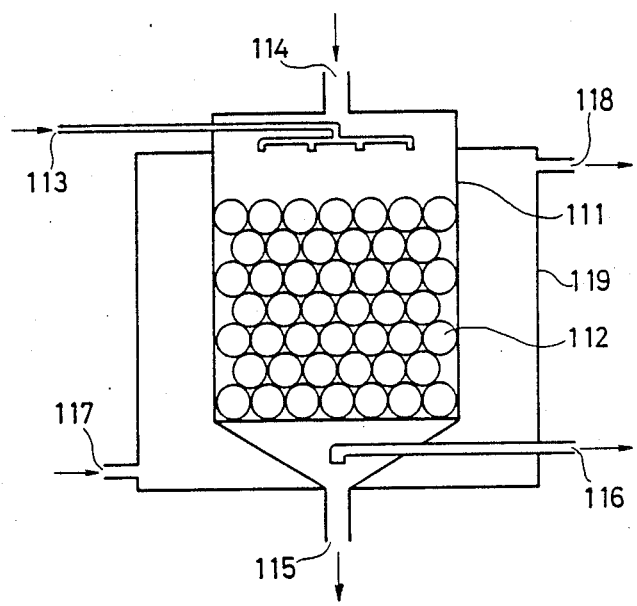
FIG. 3 shows an example of apparatuses of this invention for the manufacture of formic acid.

The apparatus shown in FIG. 3 was used in this case. Sintered glass beads 112 (diameter: 7.6 to 10.5 mm) were filled in reactor 111, an aqueous suspension of strain HU (dry cell concentration: 10.86 g/l) was added under aseptic and anaerobic conditions, the mixture was allowed to stand for 24 hours to fix the microbial cells to the glass beads, and the residual liquid was slowly withdrawn from the bottom of reactor. A gaseous substrate ($H_2/CO_2$) was fed downstream through gas inlet 114 while an aqueous solution of the composition shown in Table 2 below is being added through solution inlet 113, and the solution containing formic acid formed and unreacted gasses was recovered from the bottom of reactor. Numeral 115 is the outlet for formic-acid-containing solution, numeral 117 is the inlet for hot water controlled at 32° C., numeral 118 is its outlet, and numeral 119 is a jacket.

TABLE 2

| Composition of Feed Solution | |
| --- | --- |
| Phosphate buffer solution (0.1M) | pH 8.0 |
| NaHCO$_3$ | 40 g/l |
| Na$_2$S.9H$_2$O | 0.1 g/l |
| Triton X-100 | 2 g/l |
| Methyl viologen | 7.5 nMol/l |

Fermentation was continued at 32° C. for two weeks under the conditions given in Table 3. The result obtained is also shown in the same table.

The formic acid was analyzed by the method of Lang et al. [Lang E., Lang H., Z. Anal. Chem., 260, 8–10 (1972)], the gas composition was measured by gas chromatography, and the gas flux was measured by the soap film method.

TABLE 3

| Reactor ID | 68 mm | |
| --- | --- | --- |
| Sintered glass beads | 250 ml (bulk), approx. 70 mm high | |
| Gases at inlet | Feed rate | |
| | H$_2$ | 6056.0 ml/day |
| | CO$_2$ | 1345.6 ml/day |
| Solution feed rate | 18.0 ml/day | |

TABLE 3-continued

| Gases at outlet | Discharge rate | |
| --- | --- | --- |
| | H$_2$ | 6013.0 ml/day |
| | CO$_2$ | 1315.5 ml/day |
| Formic acid concentration in solution | 104 mMol/l | |

The conversion rate of hydrogen gas into formic acid was very high as shown in the calculation given below, $$\text{Conversion rate} = \frac{H_2 \text{ in Formic acid}}{\text{Consumed } H_2} \times 100$$
$$= \frac{(18.0/1000)(104/1000)}{(6056.0 - 6013.0)/(22400)} \times 100$$
$$= 97.5\%$$

in which the amount of hydrogen gas dissolved in solution was negligible.

What is claimed is:

1. A method for causing the fermentive transformation of a gaseous substrate into a product, comprising:
   (i) passing an aqueous solution through a reactor over microbial cells fixed onto a carrier held in said reactor, said aqueous solution being passed in an amount sufficient to moisten at least part of the surface of said microbial cells and in an amount of at most that amount needed to moisten the whole surface of said microbial cells;
   (ii) forcing a gaseous substrate through interstices between said moistened microbial cells; and
   (iii) obtaining a fermentation product.

2. The method of claim 1, comprising using a gaseous substrate which is substantially insoluble in said aqueous solution.

3. The method of claim 2, wherein said gaseous substrate contains at least one member selected from the group consisting of hydrogen, carbon dioxide, carbon monoxide, oxygen and nitrogen.

4. The method of claim 3, comprising forcing a gaseous mixture of hydrogen and carbon dioxide, at a mixing ratio of four or higher, using as said microbial cells, cells of a menthanogen, and obtaining methane as said product.

5. The method of claim 4, comprising supplying hydrogen gas, carbon dioxide gas, an aqueous solution containing methyl viologen to said methanogen and obtaining formic acid.

* * * * *